United States Patent
Appling (10) Patent No.: US 6,966,886 B2
(45) Date of Patent: Nov. 22, 2005

(54) BLOOD TREATMENT CATHETER ASSEMBLY

(75) Inventor: William M. Appling, Granville, NY (US)

(73) Assignee: AngioDynamics, Inc., Queensbury, NY (US)

(*) Notice: Subject to any disclaimer, the term of this patent is extended or adjusted under 35 U.S.C. 154(b) by 134 days.

(21) Appl. No.: 10/331,667

(22) Filed: Dec. 27, 2002

(65) Prior Publication Data

US 2004/0097863 A1 May 20, 2004

Related U.S. Application Data

(60) Provisional application No. 60/427,831, filed on Nov. 20, 2002.

(51) Int. Cl.[7] .......................... A61M 37/00; A61M 3/00; A61M 5/178; A61M 25/00
(52) U.S. Cl. .................. 604/6.16; 604/43; 604/164.01; 604/264; 604/284
(58) Field of Search ............................. 604/4.01, 6.16, 604/8, 19, 27–28, 39, 43, 500, 264, 523, 508, 528, 532, 533–4, 538, 284, 540–44, 164.01, 164.09, 164.11, 164.12, 164.13, 165.01, 165.02, 170.01, 170.02; 600/433–35; 606/191, 194; 138/115–118, 128

(56) References Cited

U.S. PATENT DOCUMENTS

| | | | |
|---|---|---|---|
| 4,134,402 A | | 1/1979 | Mahurkar |
| 4,315,512 A | | 2/1982 | Fogarty |
| 4,385,631 A | | 5/1983 | Uthmann |
| 4,619,643 A | | 10/1986 | Bai |
| 4,643,711 A | | 2/1987 | Bates |
| 5,041,083 A | | 8/1991 | Tsuchida et al. |
| 5,053,023 A | | 10/1991 | Martin |
| 5,087,247 A | | 2/1992 | Horn et al. |
| 5,106,368 A | * | 4/1992 | Uldall et al. |
| 5,267,958 A | | 12/1993 | Buchbinder et al. |
| 5,405,341 A | * | 4/1995 | Martin |
| 5,536,250 A | * | 7/1996 | Klein et al. |
| 5,718,692 A | | 2/1998 | Schon et al. |
| 5,807,311 A | * | 9/1998 | Palestrant |
| 5,947,953 A | | 9/1999 | Ash et al. |
| 6,001,079 A | | 12/1999 | Pourchez |
| 6,190,349 B1 | * | 2/2001 | Ash et al. |
| 6,695,832 B2 | * | 2/2004 | Schon et al. |
| 6,719,749 B1 | * | 4/2004 | Schweikert et al. |
| 6,743,218 B2 | * | 6/2004 | Maginot et al. |

* cited by examiner

Primary Examiner—Patricia Bianco
(74) Attorney, Agent, or Firm—Reed Smith LLP.

(57) ABSTRACT

A blood treatment catheter pre-assembled with a stiffening tube is provided. The catheter includes a withdrawal lumen and a supply lumen each having distal split tube unjoined segments and an intermediate joined segment. The split tube segment of the supply lumen is provided with a sidewall aperture. The stiffening tube extends through the withdrawal split tip tube, out the distal end of the withdrawal tube, through the aperture of the supply split tip tube and through the split tip supply tube distal of the aperture, out the distal end of the split tip supply tube. When the stiffening tube is positioned inside the catheter, the aperture is adjacent to the withdrawal tube distal opening so as to minimize stiffening tube exposure and to provide a smooth exterior profile.

23 Claims, 7 Drawing Sheets

BLOOD TREATMENT CATHETER ASSEMBLY

REFERENCE TO RELATED APPLICATIONS

This application claims the priority benefit of U.S. Provisional Application No. 60/427,831 filed Nov. 20, 2002 and entitled: Split-Tip Catheter Insertion Apparatus.

FIELD OF THE INVENTION

The present invention relates to a blood treatment catheter assembly and more particularly to a split tip, dual-tube hemodialysis catheter having enhanced ease of placement.

BACKGROUND OF THE INVENTION

Hemodialysis is a blood treatment procedure for patients with renal failure or in other cases where the kidneys cannot adequately cleanse the blood of toxins. During hemodialysis, the patient's blood is withdrawn, filtered of toxins, and returned to the blood stream. The dialysis procedure takes several hours and is done several times a week. The long hours and the frequency of the dialysis treatment in patients with renal failure requires reliable, continued access to the venous system for blood exchange. Long-term venous access mechanisms commonly used for hemodialysis treatment include vascular access ports, dialysis grafts and hemodialysis catheters.

One type of blood treatment catheters well known in the art is a dual-lumen hemodialysis catheter. These catheters are designed to provide long-term access to the venous system for dialysis. In one form, the dialysis catheter contains two lumens, a withdrawal lumen for withdrawing blood to be treated from a blood vessel and a supply lumen for returning cleansed blood to the vessel. The distal segment of the catheter is preferably positioned at the junction of the superior vena cava and right atrium to obtain a blood flow of sufficient volume to accommodate dialysis treatment requirements.

Dual lumen, split tip hemodialysis catheters are dialysis catheters in which the two lumens include two separate proximal tube segments and two separate distal tube segments. These two separate distal tip tubes are known as split tips. Split tip catheters have several advantages over unitary multi-lumen catheters. Each of the distal tube segments is capable of moving independently of the other tube and can provide fluid flow around the entire circumference of the distal ends of the catheter tubes. This fluid flow pattern decreases the likelihood of catheter occlusion with the wall of the vessel. In addition, scientific studies have indicated that the split tip catheter design may reduce the amount of fibrin or other material build-up at the distal end of the catheter.

Although superior in performance to unitary dual-lumen dialysis catheters, the split tip catheter design makes the process of inserting the catheter into the patient more complex. There are two generally accepted techniques for inserting dual-lumen, split tip dialysis catheters. One technique is to use a dilator/sheath, while the other is a guide wire weaving method.

The dilator/sheath technique is more commonly used. In that technique, split tip catheters are placed through a split-able or tear-away sheath. After accessing the target vein with a needle and guide wire, the sheath/dilator is advanced over the guide wire into the vein. Once the puncture site is sufficiently expanded, the guide wire and dilator are removed leaving only the sheath in place. The distal tip of the split tip catheter is then manually inserted into the sheath and advanced into the vein. The physician inserts both tubes into the sheath. Once the catheter is in position within the vein, the sheath is slowly pulled out while the visible portion of the sheath is simultaneously split into two.

One major problem associated with the sheath/dilator technique of insertion is the increased chance of air embolism due to the large size and location of the insertion site. An air embolism occurs when air enters the venous system through an opening caused by the insertion of the dialysis catheter. The low-pressure gradient of the venous system combined with intake of breath by the patient can create a negative pressure in the area of the puncture site. Negative pressure causes the ambient air to flow through the puncture site and into the blood stream. If air bubbles in the blood stream reach a sufficient volume, they can interfere with the normal pumping of blood by the heart, with fatal consequences.

To ensure against a possible air embolism, the physician should occlude the sheath immediately after the dilator is removed. The vein may also be exposed to air during the time required to insert the catheter into the sheath. The sheath insertion technique is further complicated by the number of medical components required to perform the procedure and the increased amount of time required to insert and remove those multiple components.

The guide wire weaving technique is another catheter insertion method known in the art. Using a direct needle stick method for access and insertion, this technique eliminates the need for a sheath. The guide wire is placed into the vein using a normal Seldinger technique. The tissue is dilated with an appropriate size dilator. The catheter is then back loaded and woven over the guide wire. In back loading, the proximal end of the guide wire is inserted into the distal most lumen of the catheter and then the guide wire is threaded out a side hole in the distal most tube and back into the other lumen of the catheter through its distal opening, effectively joining the two catheter tubes together. The catheter is then advanced over the guide wire as a single unit into the target vein.

Although the guide wire weaving method eliminates the need for a sheath, it is a cumbersome process since it requires the physician to manually thread the guide wire through the appropriate holes in the catheter prior to insertion. Another problem with this technique is the likelihood of the catheter shaft accordianing over the guide wire. Attempting to advance a soft-durometer catheter directly over a guide wire may also cause kinking and what is known in the art as accordianing. Friction between the guide wire and the inner wall of the catheter may also create difficulty during the insertion procedure.

Figure 7:
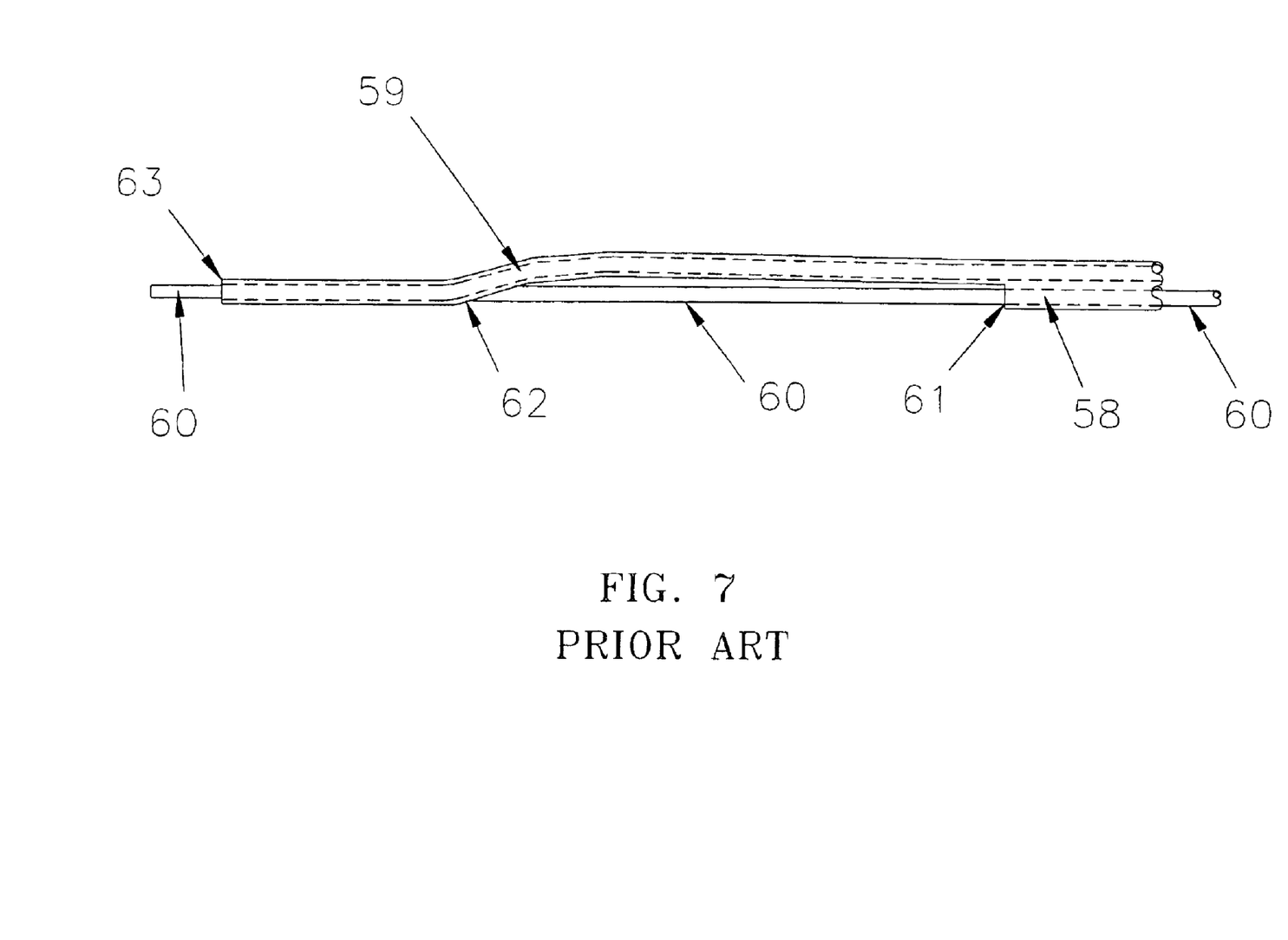
FIG. 7 is a view of the distal segment of a prior art non-split tip catheter with exposed stiffening tube 60.

In U.S. Pat. No. 5,405,341, Martin discloses a dual-lumen non split tip catheter assembly with a tubular stiffening tube for insertion using a guide wire and the Seldinger technique, a relevant portion of which is illustrated in FIG. 7 herein. Referring to FIG. 7, the unitary catheter assembly includes a first lumen 58 and a second lumen 59 which are positioned side-by-side. The lumens 58, 59 are in a unitary housing over the entire length of the first lumen 58, which is the withdrawal lumen, forming a unitary dual-lumen shaft. A stiffening tube 60 extends through the lumen 58, through the end opening 61 of lumen 58, through an aperture 62 in a distal section of the supply lumen 59 through the distal section of lumen 59 and extends out the end opening 63. This arrangement is adapted to a dual lumen catheter that is not split tip.

It is a major purpose of this invention to provide a split tip blood treatment catheter having the advantage that it is easier for the surgeon to insert into the patient.

A further purpose is to provide such a catheter that does not require a sheath for insertion because it has a design which minimizes tissue damage during placement in a patient.

It is a related purpose to provide the tissue damage minimization advantage without creating the risk of air embolism.

It is a further related purpose of this invention to provide the above objects in a design that minimizes the time and trauma associated with the placement procedure.

BRIEF DESCRIPTION

A split tip, blood treatment catheter has the two lumens in a unitary housing along an intermediate length up to a dividing point. Distal of that dividing point, the two lumens branch off from one another in two separate unjoined tubes. These two tubes have different lengths. The longer one of the two tubes supplies the filtered blood from the dialysis machine. The shorter one of the two tubes provides withdrawal of unfiltered blood from the patient for delivery to the dialysis machine. Accordingly, these two tubes will generally be referred to herein as the supply tube and withdrawal tube, respectively. These tubes are made of a highly flexible material that tends to accordian so that by themselves they cannot readily be inserted into a patient's vascular system. To enable insertion, this invention provides a stiffening tube that extends along the length of the withdrawal lumen to the distal end exit port of the withdrawal tube (the shorter of the two tubes). At that point, the stiffening tube extends through an opening in the sidewall of the supply tube and extends distal of that opening out through the end port of the supply tube.

This stiffening tube is pre-assembled with the catheter so that the assembly of catheter and stiffening tubes is ready for placement. In assembly, the stiffening tube passes immediately from the distal end of the withdrawal tube through the wall of the supply tube and holds the supply tube and withdrawal tube together.

The end of the withdrawal tube is preferably beveled so that little or none of the stiffening tube is exposed. The profile presented by the assembly of the catheter and stiffening tube is minimal and relatively smooth in that it avoids rough transitions.

Prior to use, the assembly of the catheter and stiffening tube is inserted or placed into a patient's body. The procedure for the insertion of the catheter involves a prior placement of standard type of guide wire in the vascular system of the patient by a known procedure such as the Seldinger procedure. Prior dilation using a fascial dilator may be necessary to expand the tract. The assembled catheter and stiffening tube is then inserted over the guide wire by placing the distal end of the stiffening tube over the proximal end of the guide wire and moving the catheter and stiffening tube assembly along the guide wire until the catheter is in an appropriate position within the patient's body. The guide wire is then removed and the stiffening tube is also removed leaving the catheter in place. The catheter is then ready for use in the dialysis procedure.

DESCRIPTION OF THE PREFERRED EMBODIMENTS

FIGS. 1–5 illustrate a presently preferred embodiment of the invention.

Figures 1, 1A:
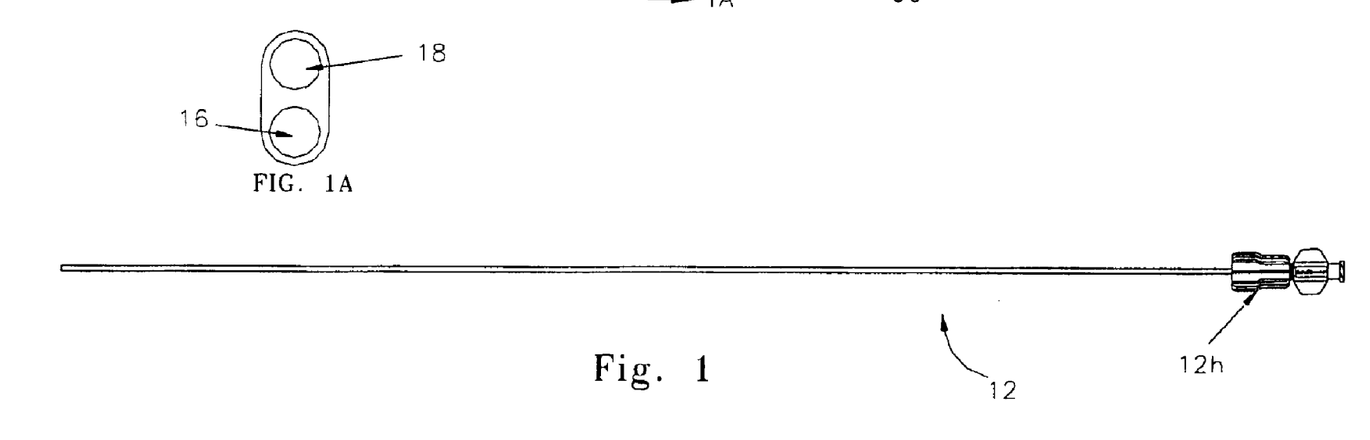
FIG. 1 shows a dual-lumen split tip catheter 10 and stiffening tube 12 according to the present invention in an unassembled configuration.
FIG. 1A is a cross-sectional view along the plane 1A—1A of FIG. 1 showing the relationship of the supply lumen 18 and withdrawal lumen 16 in the joined segment 20 of the catheter.
Figure 2:
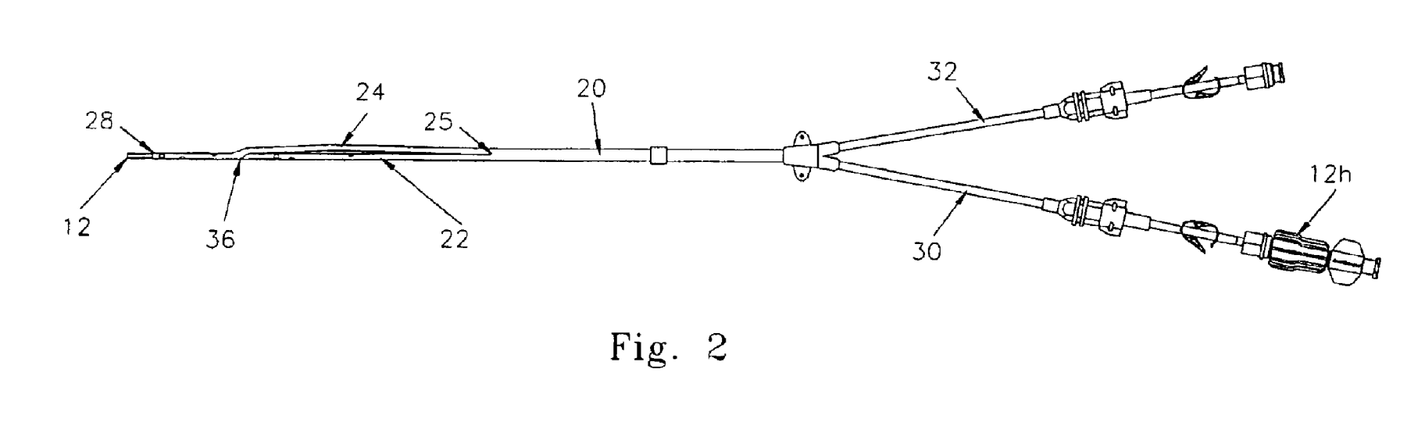
FIG. 2 shows the FIG. 1 dual-lumen, split tip catheter 10 and stiffening tube 12 assembled in which the tube 12 couples the unjoined tubes 22 and 24.

A dual-lumen split tip catheter 10 containing a stiffening tube 12 is shown unassembled in FIG. 1 and assembled in FIG. 2. The stiffening tube 12, which has been called an obturator, is generally a hollow cannula made of a plastic material such as polytetrafluoroethylene, also known as PTFE resin, sold under the trademark Teflon™ made by DuPont of Wilmington, Del. It is to be understood, however, that the stiffening tube 12 can be any longitudinal stiffening member, hollow or not, which performs the function described herein.

The stiffening tube 12 has a standard luer hub 12h at the proximal end of the device for connection to the catheter 10. The catheter 10 is comprised of a withdrawal lumen 16 and a supply lumen 18.

The withdrawal lumen 16 is the shorter lumen. It is contained within a proximal tube 30, a joined segment 20 and a distal split tube segment 22 and terminates at a distal port 26.

The supply lumen 18 is the longer lumen. It is contained within a proximal tube 32, the joined segment 20 and a distal split tube segment 24 and terminates at a distal port 28.

Distal to the dividing point 25 of the joined segment 20, the withdrawal lumen 16 includes a split tube 22 and the supply lumen 18 includes a split tube 24. The split tubes 22, 24 terminate, respectively, at distal opening 26 and 28. The withdrawal lumen 16 performs a blood withdrawal function. It receives un-dialyzed blood through distal opening 26. The uncleansed blood enters distal opening 26, travels through the withdrawal tube 22, the segment 20 and the proximal tube 30 and exits through a connector 34 which is attached to a dialysis machine (not shown). Toxins in the blood are removed by the dialysis machine and the clean blood is returned to the catheter 10 through a supply connector 35.

The cleansed blood travels through a proximal tube 32 of the supply lumen 18, flows through the joined dual lumen segment 20, continues through the supply split tube 24 and exits through the distal supply opening 28 into the bloodstream.

The sizes of the catheter inner diameter and stiffening tube 12 outer diameter are selected to provide sufficient friction between the Teflon tube 12 and the inner catheter wall to reduce the likelihood of accordianing or buckling from compression during insertion. The friction between the catheter and tube 12 is not so great as to prevent easy withdrawal of the tube 12 after the catheter has been positioned in the vein.

In one embodiment, when assembled, the stiffening tube 12 extends one to three cm distal of the end opening 28 of the supply tube 24. In that embodiment, the withdrawal lumen 16 and supply lumen 18 have a diameter of approximately 0.078 inches (78 mils). The outside diameter of the supply tube 24 and withdrawal tube 22 is 0.125 inches (125 mils). In that embodiment, the stiffening tube 12 has an outside diameter of 0.075 inches (75 mils) and an inside diameter of 0.042 inches (42 mils) and is made of PTFE resin (Teflon™ from DuPont).

Figures 3, 3A, 3B:
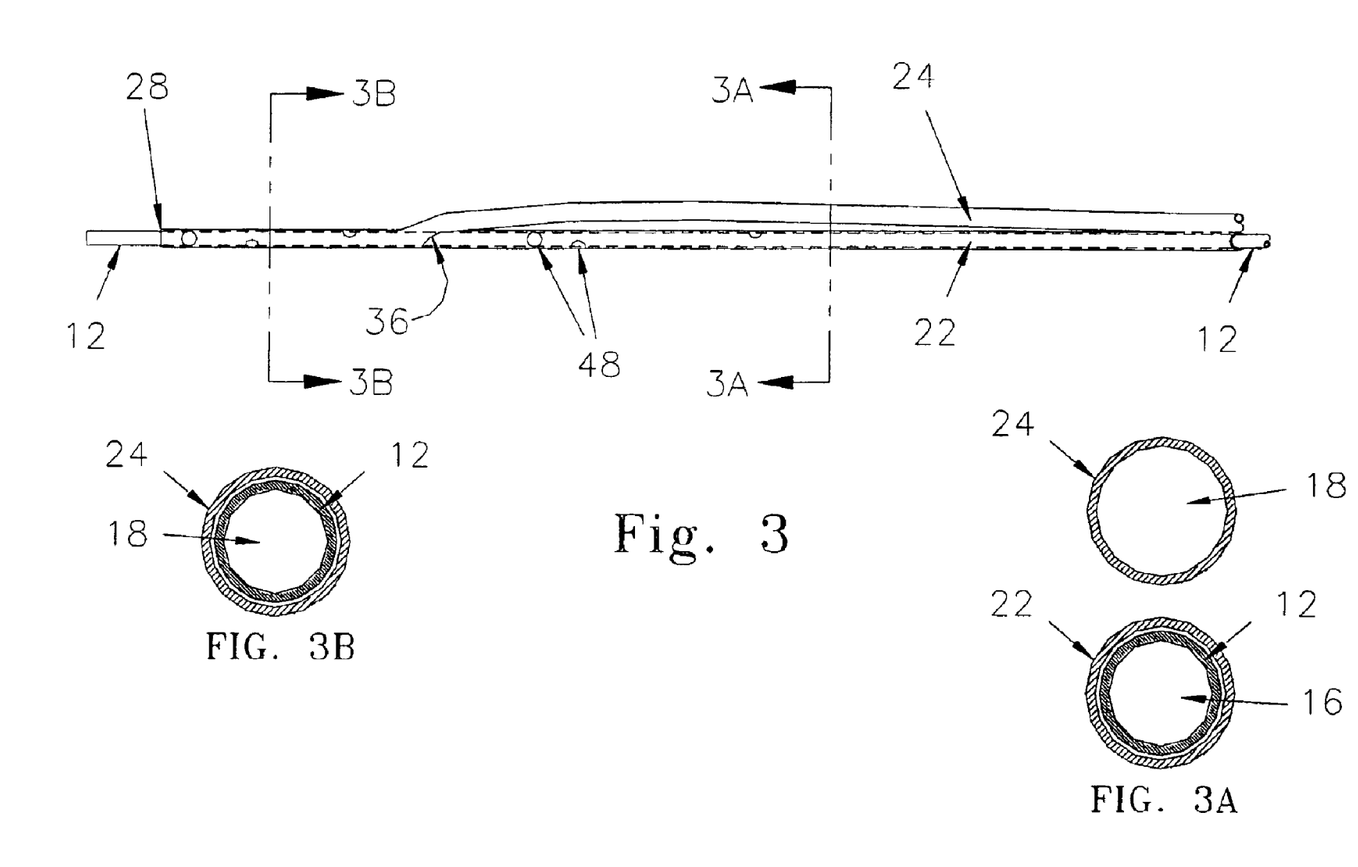
FIG. 3 is an enlarged view of the distal segment of the FIG. 2 assembly of catheter and stiffening tube.
FIG. 3A is a cross-sectional view along the plane 3A—3A of FIG. 3 showing the relationship of the split tube segments 22 and 24 when the stiffening tube 12 is in place.
FIG. 3B is a cross-section along the plane 3B—3B in FIG. 3 showing the stiffening tube 12 in the distal most portion of the supply lumen 18 split segment 24.

FIGS. 2 and 3 depict the catheter 10 assembled with the stiffening tube 12. The stiffening tube 12 extends through the entire withdrawal lumen 16 (which is the shorter lumen that withdraws blood from the patient for dialysis cleaning) and through a distal portion of the supply lumen 18 split tube 24. In this fashion, the unjoined tubes 22, 24 are coupled for the purpose of facilitating placement in a patient.

The supply split tube 24 (which is the longer tube that provides cleansed blood to the patient) has a sidewall aperture 36 preferably in the form of a slit. The aperture 36 is positioned adjacent to the end opening 26 (FIG. 1) of the withdrawal tube 22. The stiffening tube 12 extends out the end opening 26 into the slit aperture 36 and down the rest of the lumen of the supply split tube 24 to exit at the distal end opening 28 of the split tube 24.

In the application of this invention to a dialysis catheter, it is usual for the shorter tube 22 with lumen 16 to be used to withdraw blood from the patient and the longer tube 24 with lumen 18 to supply filtered blood to the patient. Accordingly, the tubes are referred to herein as the withdrawal tube 22 and the supply tube 24. It is possible for the catheter to be connected to the dialysis machine so that the longer tube is the withdrawal tube and the shorter tube is the supply tube.

As shown in FIG. 3, the sidewall aperture 36 is positioned to be adjacent to the distal end of the withdrawal split tube 22. It is desirable that there be a minimum gap between the distal opening of the withdrawal tube 22 and the aperture 36 in the sidewall of the supply tube segment 24 so that during placement in a patient there will be minimum accordianing of the supply tube segment 24 at the zone around the juncture between the tubes at the aperture 36. The less the stiffening tube 12 is exposed in that zone, the less opportunity there will be for any accordianing of the tube 24.

Figure 4:
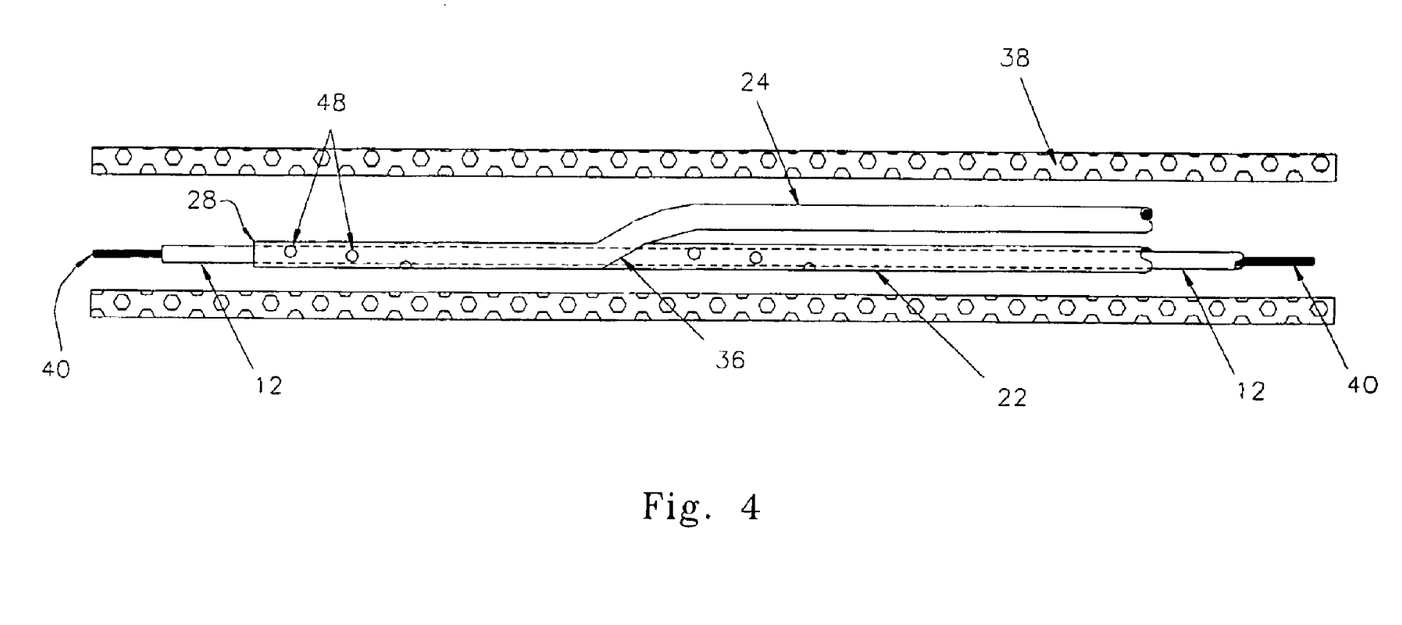
FIG. 4 shows the FIG. 3 segment positioned over a guide wire 40 within a vein 38 prior to removal of the stiffening tube 12 and guide wire.

FIG. 4 is an enlarged view of the distal portion of the catheter 10 assembled with the stiffening tube 12 within a vein 38. The assembly shows the stiffening tube 12 within the withdrawal tube 22 and within the supply tube 24 distal of the slit aperture 36. This design provides for a smooth outer catheter profile to minimize the likelihood of tissue damage that may be caused by rough transitions in the surface of the catheter assembly.

Figure 5:
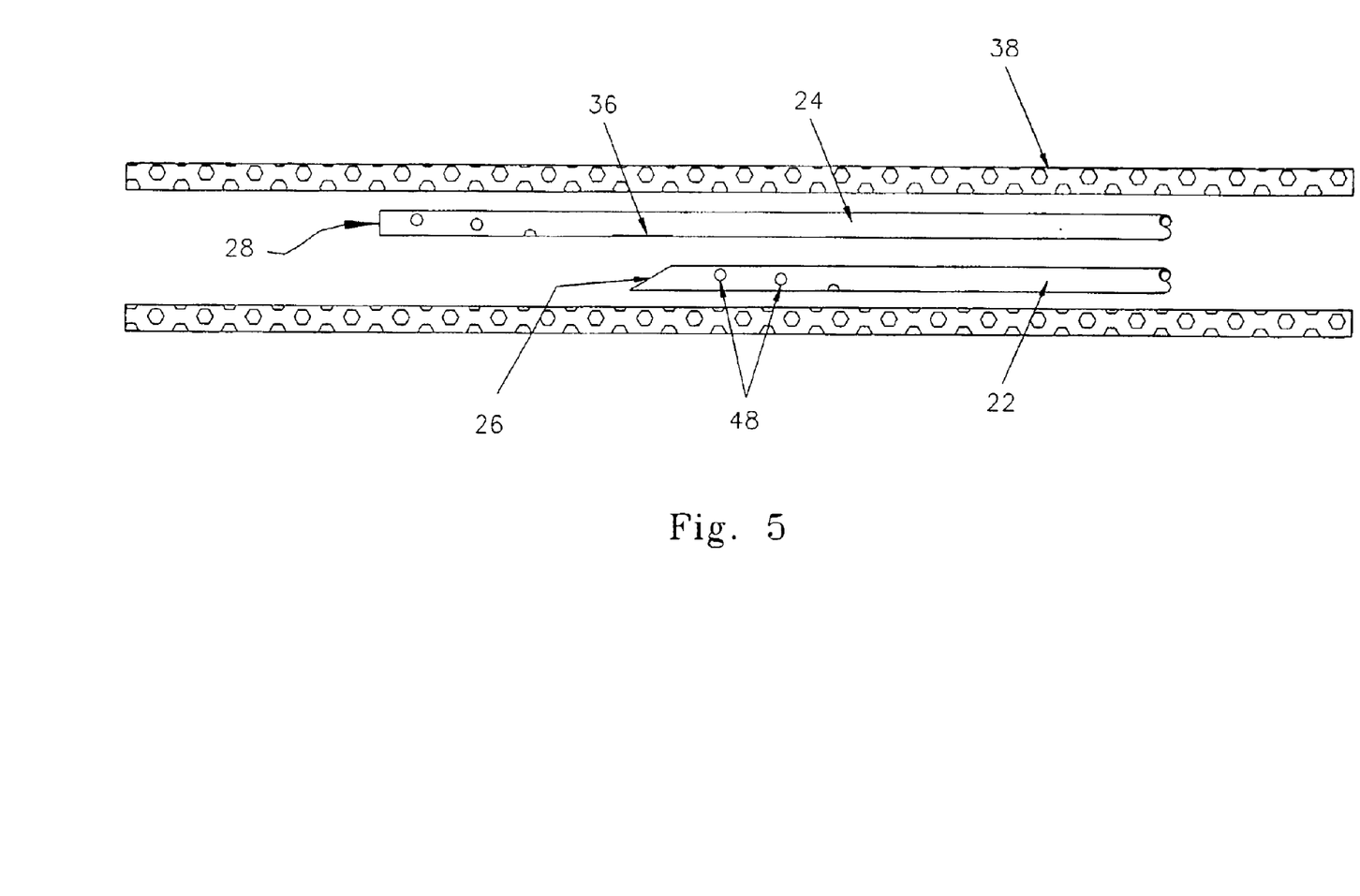
FIG. 5 is a view similar to that of FIG. 4 after the guide wire 40 and stiffening tube 12 have been removed. This is the operating state of the catheter in which the unjoined tubes 22 and 24 are uncoupled.

As may be seen in FIG. 5, in a preferred embodiment the distal end at the opening 26 is beveled or chamfered at an angle of approximately 30 degrees to the axis of the tube 22 to facilitate engagement between the open end 26 of the tube 22 and the slit aperture 36 and to assure that the stiffening tube 12 is preferably not exposed so that the transition at the juncture between the opening 26 and aperture 36 is relatively smooth and avoids rough transitions in the external configuration of the catheter. However, a straight cut open end 26 can be effectively used.

This design also creates a profile that allows for gradual dilation of the insertion track during advancement of the catheter assembly into the vein.

The distal withdrawal opening 26 as shown in FIG. 5 is angled at 30 degrees with respect to the longitudinal axis of tube 22. When assembled with the stiffening tube 12, the angled configuration ensures that the withdrawal opening 26 fits flush against the outer surface of the split tube 24 at the sidewall aperture slit 36. This design minimizes exposure of the stiffening tube 12, as shown in FIG. 4, to assure the smooth transition discussed above. The bevel at the distal withdrawal opening provides an opening which faces away from the vessel wall in which the catheter is inserted. This minimizes the risk of the withdrawal tube 22 being suctioned against the vessel wall 38 during dialysis which avoids the problems of reduced flow rate and damage to the vessel wall. The slit aperture 36 is positioned to face the beveled opening 26. FIG. 5 shows the aperture 36 displaced from the optimum positioning in order to provide a visible indication of the aperture in FIG. 5.

The stiffening tube 12 provides rigidity and pushability to the catheter 10 during insertion. The internal diameter of the stiffening tube 12 is of a size that can readily pass over a guide wire 40.

The catheter shaft is preferably made of a soft durometer urethane material. The urethane material and soft durometer create a relatively high coefficient of friction between the inner wall of the catheter shaft and the guide wire 40. The stiffening tube 12 is comprised of materials that create a reduced coefficient of friction between the guide wire 40 and stiffening tube inner wall. As a result, advancing the catheter/stiffening tube assembly 10, 12 over the guide wire 40 is easily accomplished, which reduces the likelihood of the catheter accordianing or developing kinks.

Figure 6:
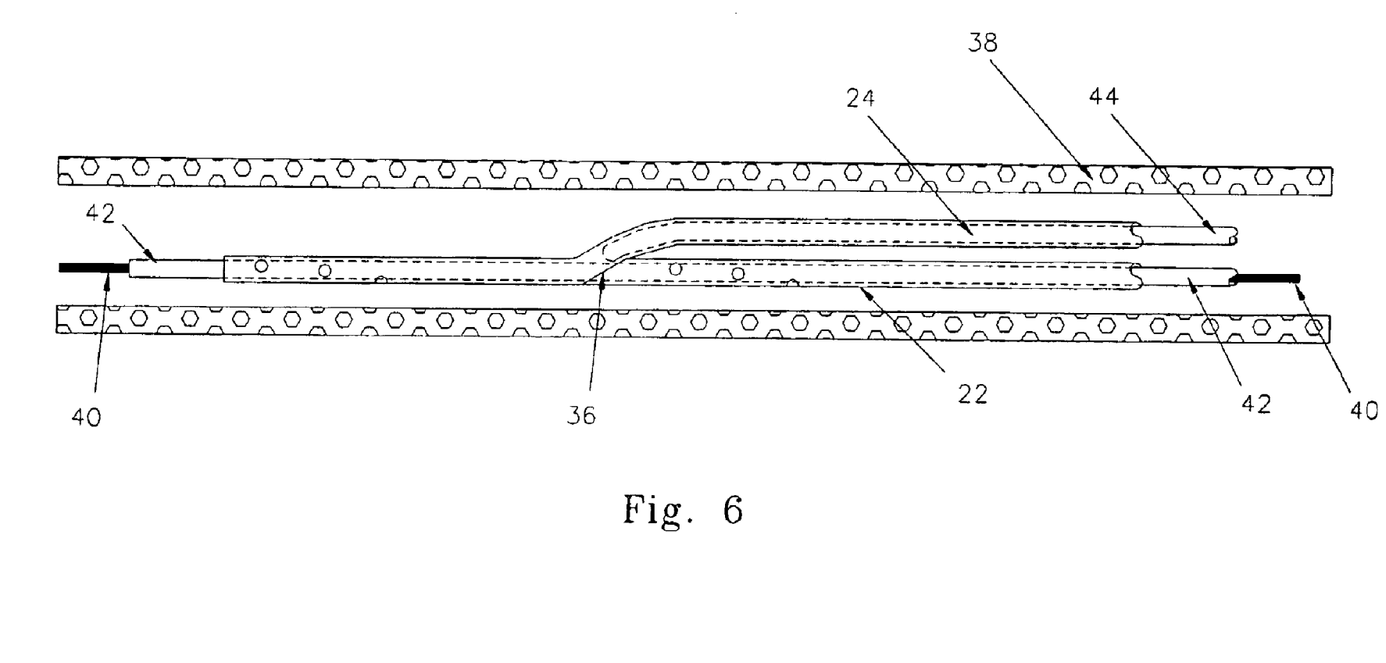
FIG. 6 is a view similar to that of FIG. 4 of a second embodiment having two stiffening tubes 42 and 44.

In another embodiment of the present invention, the catheter assembly includes two stiffening tubes 42, 44 one in each catheter tube as depicted in FIG. 6. The first stiffening tube 42 is positioned within the withdrawal lumen 16 and extends into the supply tube 24 distal of the aperture 36 in the fashion described with reference to FIGS. 2–4. A second stiffening tube 44 is inserted into the supply lumen 18 until it is just proximal to the aperture 36 on the supply split tube 24. The second stiffening tube 44 provides additional pushability and rigidity to the catheter shaft during insertion. The second stiffening tube 44 does not have to be designed to pass over a guide wire.

The stiffening tubes 42 and 44 are dimensioned such that when inserted into the corresponding catheter lumen, the proximal end of the stiffening tubes will lock into the withdrawal and supply connectors of the catheter. When locked to the withdrawal connector, the first stiffening tube 42 is of sufficient length to protrude out of the distal supply lumen and opening by between 0.5 cm and 2 cm, preferably 1 cm. The second stiffening tube 44 is of a length such that when locked to the supply tube connector, the distal end of the second stiffening tube 44 is located proximal to the position of the aperture 36.

Placement in a Patient

Once the catheter/stiffening tube assembly 10, 12 has been positioned over a guide wire 40 within the superior vena cava vein to the physician's satisfaction, the guide wire 40 and stiffening tube 12 are removed. Upon removal, the unjoined split tubes 22 and 24 of the catheter will separate within the vein vessel. The split aperture 36 on the supply tube 24 will automatically return to a substantially closed configuration when the stiffening tube 12 is removed. The slit design is preferable to minimize the amount of dialyzed blood that returns through the aperture 26.

The present invention does not require a peel-away or other type of sheath. The stiffening tube 12 is pre-assembled in the catheter 10 as shown in FIGS. 2 and 3. The catheter/stiffening tube assembly is packaged in that pre-assembled configuration. The stiffening tube 12 is woven into position through the catheter 10 during manufacture. The physician inserts the assembly into the puncture site in a single step by advancing the catheter assembly over a guide wire.

Insertion of the catheter/stiffening tube assembly depicted in FIG. 2 into the vein is achieved with a Seldinger technique. An introducer needle is inserted into the jugular or subclavian vein. The guide wire 40 is inserted through the needle into the vein. The needle is then removed. The insertion track is enlarged by a tissue dilator of the appropriate size. A small incision is made on the anterior chest wall. A subcutaneous tunnel is created between this incision and the guide wire exit site. The catheter 10, pre-assembled with the stiffening tube 12, is inserted into the anterior chest wall incision and passed through the tunnel exiting near the guide wire 40. The stiffening tube 12 provides stiffness to the catheter assembly during the advancement through the subcutaneous tunnel. The dilator is then removed. The proximal end of the guide wire 40 is back loaded into the distal end of the exposed stiffening tube 12 and then the catheter/stiffening tube assembly is advanced through the puncture site and into position within the vein.

The stiffening tube 12 provides the stiffness or body to advance the catheter 10 through the puncture site without creating an oversized diameter puncture site. This insertion method for dialysis catheters reduces the risk of air embolisms because the insertion site is smaller and the time period in which the puncture is exposed to air is reduced because the time required to complete the procedure with the steps involving the sheath are eliminated.

Once the catheter assembly is positioned correctly within the vein, the guide wire 40 is removed. After guide wire removal, the stiffening tube 12 is unlocked from the withdrawal connector 34 (FIG. 1) and withdrawn from the catheter 10 through the subcutaneous tunnel. Removing the stiffening tube 12 releases the catheter supply and withdrawal tubes 24 and 22 from their coupled position shown in FIG. 4 to the uncoupled position shown in FIG. 5.

The stiffening tube/catheter assembly can also be used to facilitate insertion using a sheath without a guide wire. In this procedure, the stiffening tube 12 is woven through the catheter 10 as previously described and depicted in FIG. 2. The distal end of stiffening tube/catheter assembly is inserted directly into the proximal hub of the sheath and advanced until properly positioned within the vein. Use of the stiffening tube 12 facilitates insertion by providing the additional stiffness needed to advance the catheter 10 through the sheath. The stiffening tube 12 also provides the function of joining the unjoined distal tubes 22 and 24 together to form a temporary combined structure, thus preventing individual movement and possible kinking of these tubes 22, 24 during advancement.

While certain novel features of this invention have been shown and described above, the present invention may be embodied in other specific forms without departing from the spirit or essential characteristics of the invention. The described embodiments are to be considered in all respects only as illustrative and not as restrictive. Various omissions, modifications, substitutions and changes in the forms and details of the device illustrated and in its operation can be made by those skilled in the art without departing in any way from the spirit of the present invention. For example, the following two definitions should be kept in mind when reviewing the claims.

Stiffening Tube

The stiffening tube 12 provides a stiffening function to the assembly of the tube 12 with the catheter 10. By itself, the tube 12 need not be particularly stiff. The tube 12 in combination with the catheter gives greater body to the pre-woven assembly of the stiffening tube 12 and catheter 10 so that the pre-woven assembly can be readily passed over a guide wire and placed in a patent. The stiffening tube 12 is preferably a tube and performs a stiffening function for the assembly of soft-durometer catheter tubes and stiffening tube. Although it is preferably tubular so that it can be fed over a guide wire, it should be understood that the term stiffening tube refers to any longitudinal stiffening member including a solid rod. There are possible applications of the invention where the stiffening tube is a rod, when the catheter is advanced into place in the patient's body without the use of a guide wire. For example, when a sheath is employed, the guide wire may not be necessary.

Sidewall Aperture

The sidewall aperture 36 in the longer of the two separate split tip tubes, which has the supply tube 24, is preferably in the form of a slit on the sidewall. It is this slit 36 through which the stiffening tube 12 is inserted so as to cause the appropriate joining of the split segments 22 and 24 of the lumens 16 and 18 during the step of placing the catheter in the patient. When the stiffening tube 12 is removed, the slit opening substantially recloses. However, a sidewall opening may remain, or indeed the aperture may be created with a sidewall opening. In the sidewall opening embodiment of the aperture 36, the opening has to be sufficiently great to accept the stiffening rod 12 and can even be large enough to accommodate the distal end of the tube 22. Smaller sidewall openings 48 at the distal portions of the two unjoined tubes 22 and 24 are normally incorporated in order to assure adequate flow rate. As is known in the art, there is some trade-off between a design for adequate flow rate and a design for minimum recirculation.

As another example, the joined intermediate segment 20 is preferably a single housing for the two lumens 16 and 18. However, two individual tubes could be employed throughout the length of the catheter, which tubes are joined together at an intermediate segment.

What is claimed is:

1. A blood treatment catheter comprising:
   first and second lumens, said lumens being in a joined segment proximal to a dividing point and in first and second unjoined tubes, respectively, distal of said dividing point, said first tube having a length greater than the length of said second tube,
   an aperture on the sidewall of said first unjoined tube at a distance distal of said dividing point, and
   a stiffening tube extending through the catheter, said stiffening tube passing through said second unjoined tube, through said aperture and extending distally of said aperture through said first unjoined tube;

wherein said aperture is at a position on said first unjoined tube a distance distal of said dividing point that is substantially equal to the length of said second unjoined tube.

2. The catheter according to claim 1 wherein: the catheter is a hemodialysis catheter and said first lumen is a blood supply lumen and said second lumen is a withdrawal lumen.

3. The catheter according to claim 2 further comprising: a beveled distal end of said second unjoined tube, said beveled end being positioned to facilitate placing said distal end of said second unjoined tube at said aperture.

4. The catheter according to claim 1 wherein: the catheter is a hemodialysis catheter and said first lumen is a blood supply lumen and said second lumen is a withdrawal lumen.

5. The catheter according to claim 4 further comprising: a beveled distal end of said second unjoined tube, said beveled end being positioned to facilitate plating said distal end of said second unjoined tube at said aperture.

6. The catheter according to claim 1 further comprising: a beveled distal end of said second unjoined tube, said beveled end being positioned to facilitate placing said distal end of said second unjoined tube at said aperture.

7. The catheter according to claim 1 further comprising: a beveled distal end of said second unjoined tube, said beveled end being positioned to facilitate placing said distal end of said second unjoined tube at said aperture.

8. A blood treatment catheter comprising:
first and second lumens, said lumens being in a joined segment proximal to a dividing point and in first and second unjoined tubes, respectively, distal of said dividing point, said first tube having a length greater than the length of said second tube,
an aperture on the sidewall of said first unjoined tube at a distance distal of the dividing point; and
a stiffening tube extending through the catheter, said stiffening tube passing through said second unjoined tube, through said aperture and extending distally of said aperture through said first unjoined tube;
said stiffening tube being minimally exposed in a transition zone between said first and second unjoined tubes;
wherein said aperture is at a position on said first unjoined tube a distance distal of said dividing point that is substantially equal to the length of said second unjoined tube.

9. The catheter according to claim 8 wherein: the catheter is a hemodialysis catheter and said first lumen is a blood supply lumen and said second lumen is a withdrawal lumen.

10. The catheter according to claim 9 further comprising: a beveled distal end of said second unjoined tube, said beveled end being positioned to facilitate placing said distal end of said second unjoined tube at said aperture.

11. The catheter according to claim 8 wherein: the catheter is a hemodialysis catheter and said first lumen is a blood supply lumen and said second lumen is a withdrawal lumen.

12. The catheter according to claim 11 further comprising: a beveled distal end of the second unjoined tube, said beveled end being positioned to facilitate placing said distal end of said second unjoined tube at said aperture.

13. The catheter according to claim 8 further comprising: a beveled distal end of said second unjoined tube, said beveled end being positioned to facilitate placing said distal end of said second unjoined tube at said aperture.

14. The catheter according to claim 8 further comprising: a beveled distal end of said second unjoined tube, said beveled end being positioned to facilitate placing said distal end of said second unjoined tube at said aperture.

15. A hemodialysis catheter comprising:
supply and withdrawal lumens positioned within a joined segment proximal to a dividing point and located in first and second unjoined tubes distal of said dividing point, said first unjoined tube containing said supply lumen having a length greater than the length of said second unjoined tube having said withdrawal lumen,
an aperture on the sidewall of said first unjoined tube at a distance distal of said dividing point, and
a stiffening tube extending through the catheter, said stiffening tube passing through said second unjoined tube, through said aperture and extending distally of said aperture through said first unjoined tube,
said stiffening tube being minimally exposed in a transition zone between said first and second unjoined tubes;
wherein said aperture is at a position on said first unjoined tube a distance distal of said dividing point that is substantially equal to the length of said second unjoined tube.

16. The catheter according to claim 15 further comprising: a beveled distal end of said second unjoined tube, said beveled end being positioned to facilitate placing said distal end of said second unjoined tube at said aperture.

17. The hemodialysis catheter according to claim 16 wherein: when the stiffening tube is removed while the catheter is positioned in a blood vessel, said beveled end faces away from the vessel wall to prevent said second tube from being suctioned against the vessel wall.

18. The hemodialysis catheter of claim 15 wherein: said aperture is a slit that substantially recloses when said stiffening tube is withdrawn.

19. The hemodialysis catheter according to claim 15 further comprising: a second stiffening tube extending through said first lumen proximal of said dividing point.

20. The method of placing a blood treatment catheter in the patient wherein the catheter has first and second lumens in a joined segment proximal to a dividing point and having the first and second lumens in first and second unjoined tubes distal of the dividing point, the first tube having a length greater than the length of the second tube, comprising the steps of:
providing a stiffening tube extending through the second tube and through an aperture in the sidewall of the first tube and extending distally of said aperture through the first tube to couple said tubes, said stiffening tube being minimally exposed in a transition zone between the first and second tubes to provide an assembly of a catheter and stiffening tube wherein the first and second unjoined tubes are coupled together, said aperture being at a position on said first unjoined tube a distance distal of said dividing point that is substantially equal to the length of said second unjoined tube,
inserting said assembly in a patient until the ends of the catheter are at a desired location within the patient, and
withdrawing the stiffening tube from the assembly to uncouple the first and second tubes.

21. A blood treatment catheter comprising:
first and second lumens, said lumens being in a joined segment proximal to a dividing point and in first and second unjoined tubes, respectively, distal of said dividing point, said first tube having a length greater than the length of said second tube,
an aperture on the sidewall of said first unjoined tube at a distance distal of said dividing point, and
a stiffening tube capable of passing through said second unjoined tube, through said aperture and extending distally of said aperture through said first unjoined tube;

wherein said aperture is at a position on said first unjoined tube a distance distal of said dividing point that is substantially equal to the length of said second unjoined tube.

22. The catheter of claim 21 wherein:

the catheter is a hemodialysis catheter and said first lumen is a blood supply lumen and said second lumen is a withdrawal lumen.

23. The catheter of claim 21 further comprising: a beveled distal end of said second unjoined tube, said beveled end being positioned to facilitate placing said distal end of said second unjoined tube at said aperture.

* * * * *